(12) United States Patent
Bridgeman

(10) Patent No.: US 6,200,607 B1
(45) Date of Patent: Mar. 13, 2001

(54) PHARMACEUTICAL COMPOSITION COMPRISING AT LEAST TYROSINE AND AN IRON COMPOUND FOR TREATING PARKINSON'S DISEASE OR DEPRESSION

(76) Inventor: Keith Bridgeman, 19 Westminster Close, Eastbourne, East Sussex BN22 OLQ (GB)

(*) Notice: Subject to any disclaimer, the term of this patent is extended or adjusted under 35 U.S.C. 154(b) by 0 days.

(21) Appl. No.: 09/367,851

(22) PCT Filed: Jan. 27, 1998

(86) PCT No.: PCT/GB98/00229

§ 371 Date: Sep. 13, 1999

§ 102(e) Date: Sep. 13, 1999

(87) PCT Pub. No.: WO98/32464

PCT Pub. Date: Jul. 30, 1998

(30) Foreign Application Priority Data

Jan. 28, 1997 (GB) .................................................. 9701675

(51) Int. Cl.⁷ .......................... A61K 33/32; A61K 33/26; A61K 31/495; A61K 31/44; A61K 31/195
(52) U.S. Cl. .......................... 424/643; 424/648; 514/249; 514/345; 514/355; 514/567
(58) Field of Search .................................... 424/643, 648; 514/249, 345, 355, 567

(56) References Cited

U.S. PATENT DOCUMENTS

| | | | | |
|---|---|---|---|---|
| 4,167,564 | * | 9/1979 | Jensen | .................................. 424/177 |
| 5,122,461 | * | 6/1992 | Hsiung et al. | ........................ 435/106 |

FOREIGN PATENT DOCUMENTS

| | | | |
|---|---|---|---|
| 4137944 | * | 5/1992 | (DE) . |
| 2617711 | * | 7/1987 | (FR) . |
| 2268871 | * | 1/1994 | (GB) . |
| 2292522 | * | 2/1996 | (GB) . |
| 94381 | * | 4/1988 | (RU) . |

OTHER PUBLICATIONS

WPI/Derwent Abstract of Japanese 07 330583 (Aug. 1996).*
WPI/Derwent Abstract of Japanese 58 162515 (Sep. 1983).*
WPI/Derwent Abstract of Romanian 94381 (Apr. 1988).*

* cited by examiner

Primary Examiner—Raymond Henley, III

(57) ABSTRACT

A pharmaceutical product comprises the use of a combination of tyrosine and iron for separate, sequential or simultaneous administration for the treatment of Parkinson's disease or depression. In a preferred embodiment the product also contains at least one of a vitamin B6 (e.g. pyridoxine), a folate (e.g. folic acid), a vitamin B3 (e.g. nicotinamide), or zinc. The product enables the natural biosynthesis, secretion, transport and action of dopamine.

32 Claims, No Drawings

PHARMACEUTICAL COMPOSITION COMPRISING AT LEAST TYROSINE AND AN IRON COMPOUND FOR TREATING PARKINSON'S DISEASE OR DEPRESSION

This is a 371 of PCT/GB98/00229 filed Jan. 27, 1998.

The invention herein relates to the treatment of Parkinson's disease and/or depression.

Parkinson's disease is a medical disorder whose characteristic symptoms are due to excessive muscle contraction. This often begins as a tremor, which can develop into muscle rigidity, and then to a complete lack of physical movement. Usually, it does not develop until adulthood and becomes progressively more common with age.

It is caused by the insufficient action of dopamine, which normally acts by preventing excessive muscle contraction. Although dopamine is produced in the dopaminergic neurons in the brain, it is not normally administered to treat the disorder since dopamine does not easily pass between the blood brain barrier.

Some existing methods of treating Parkinson's disease make use of dopamine agonists, which mimic the action of dopamine. However, though the use of dopamine agonists can be effective for a while they can cause side effects, and their long term use leads to the progressive desensitisation of the receptors that respond to them.

L-Tyrosine was compared against the use of prominent products for Parkinson's disease and was found to be more effective (Comples Rendus Academie des sciences (III) [1989] 309 (2):43–47). The use of iron in the treatment of Parkinson's disease was compared against existing methods of treatment and was found to be beneficial in all patients tested (Journal of Neural Transmission [1986] 67:287–292). Zinc deficiency has been shown to lead to, amongst other things, symptoms of Parkinson's disease. It has been reported that nicotinamidadenine dinucleotide (NADH) can be beneficial in the treatment of Parkinson's disease (Annals of Clinical and Laboratory Science [1989] 19 (1):38–43). Tetrahydrobiopterin ($BH_4$) was also found to have a therapeutic effect on Parkinson's disease patients. (Advances in Neurology 40:463–466 and Proceedings Japan Academy series B [1982] 58:283–287).

In the early 1940's a number of studies were reported to have been carried out primarily in the USA in which pyridoxine was linked to improvements in Parkinson's disease. (Minnesota Medical Association [1940] 23:542, Journal of the American Medical Association [1940] 115:839, Minnesota Medicine [1940] 23:542, Journal of the American Medical Association [1941] 116:1895, and New York State Medical Journal [1941] 41:461).

Mental depression (depressive disorders, depressive illnesses) and manic depressive disorders consist of a group of common psychiatric disorders characterised by both mental and somatic symptoms. Treatment includes psychotherapy, electroconvulsive therapy (ECT) and anti-depressant drugs such as the manoamine oxidase inhibitors, serotonin reuptake inhibitors and noradrenaline reuptake inhibitors.

It has been reported that a lack of dopamine will cause mental depression. Nicotinamide and similar substances such as nicotinic acid have been used with a fair degree of success in the treatment of depression (Canadian Psychiatric Association [1971] 16:413). Pyridoxine has been used in the treatment of depression, and was shown in certain types of cases to be successful (The Lancet [1973]:897). The deficiency of folic acid folates has been shown to result in depression (Psychological Medicine [1992] 22:871).

At present, the most common basis for the treatment of Parkinson's disease is the administration of L-dopa. L-dopa is metabolised to dopamine in vivo and, unlike dopamine, L-dopa can pass the blood brain barrier. However, its administration, via feedback inhibition causes a correspondingly reduced production of the body's own dopamine. Therefore although the use of L-dopa can initially be effective in treating Parkinson's disease, over time it leads to the condition becoming progressively worse. There are also side effects caused by the use of L-dopa.

It is an object of the inventions to provide an effective treatment for Parkinson's disease and depression, and particularly more effective than L-dopa.

It is a further object to obviate or mitigate the disadvantages of treatment with L-dopa.

According to the first aspect of the present invention there is provided the use of a combination pharmaceutical product of at least tyrosine or a pharmacologically acceptable derivative thereof and an iron containing compound in the preparation of medicament for the treatment or prophylaxis of Parkinson's disease and depression. The combination can be given separately, sequentially, simultaneously or as a combined unitary drug product. Thus for example, a blister pack containing iron and tyrosine as separate tablets to be given together would be within the scope of the invention. However a unitary tablet or capsule containing the combination is preferred.

A second aspect of the invention provides a pharmaceutical product comprising tyrosine or a pharmacologically acceptable derivative thereof together with an iron containing compound for combined, separate, sequential or simultaneous administration for the treatment or prophylaxis of Parkinson's disease or depression.

Unlike L-dopa, the invention can be used long term without significant side effects since it enables the natural biosynthesis, secretion, transport and action of the body's own dopamine.

By pharmacologically acceptable derivative of tyrosine, we mean to include any precursor which will metabolise to tyrosine in vivo such as phenylalanine (typically the L-phenylalanine). Ideally, L-tyrosine or DL-tyrosine and salts is administered in accordance with the invention. A suitable daily dosage of tyrosine (typically L-tyrosine) or derivative in accordance with the invention is 240 mg to 6000 mg, preferably 1200 mg to 3600 mg, typically about 2400 mg.

Iron should also be available in vivo with tyrosine and so any compounds or element which delivers iron in vivo is an iron containing compound in accordance with the invention. Preferably the iron containing compound contains ferrous iron (e.g. ferrous sulphate or a ferri-ferro complex e.g. oxyferriscarbone™) since this appears to be absorbed better by the body. Ferrous iron is used in the biosynthesis of dopamine. Suitable total daily dosage of iron in an iron containing compound is 2 mg to 100 mg, preferably 10 mg to 30 mg, typically about 20 mg iron. If the iron is present as iron sulphate then the weight of iron containing compound would be higher such as 54 mg ferrous sulphate (corresponding with 20 mg $Fe^{3+}$)

Preferably the combination product of the invention also comprises for separate, sequential, simultaneous administration or administration as a combined preparation, at least one of a vitamin B6 (e.g. pyridoxine), a folate (e.g. folic acid), a vitamin B3 (e.g. nicotinamide) or a zinc containing compound.

Advantageously, the combination of the invention comprises at least one vitamin B6 such as pyridoxal and pyridoxamine. However, most preferably the vitamin B6 is substantially pryridoxine or a pharmacologically acceptable salt thereof such as pyridoxine hydrochloride. Suitably the total daily dose of vitamin B6 (such as pyridoxine) is 0.2 mg to 240 mg, more preferably 1.2 mg to 3.6 mg, typically about 2.4 mg.

It is further preferred that a folate is administered in the combination of the invention. Most preferably folic acid is used. A suitable total daily dose of folate (such as folic acid) is 0.04 mg to 10 mg, preferably 0.2 mg to 0.8 mg, typically 0.4 mg.

Further preferably at least one vitamin B3 such as nicotinic acid is present in the combination of the invention, but ideally nicotinamide is present. A suitable total daily dose of vitamin B3 (such as nicotinamide) is 2 mg to 500 mg, preferably 10 mg to 30 mg, typically 20 mg.

Yet further preferably, a zinc containing compound such as zinc sulphate is also present in the combination of the invention, so as to deliver $Zn^{2+}$ in vivo. A suitable daily dose of a zinc containing compound is 2 mg to 80 mg, preferably 10 mg to 30 mg, typically 20 mg (which corresponds to 50 mg zinc sulphate).

Where a derivative of a compound of the combination is mentioned, we mean to include salts, esters, amides and other precursors which will metabolise to the compound of interest in vivo.

Suitable salts include those formed with both organic and inorganic acids. Such acid addition salts will normally be pharmaceutically acceptable although salts of non-pharmaceutically acceptable salts may be of utility in the preparation and purification of the compound in question. Thus, for example, salts include those formed from hydrochloric, hydrobromic, sulphuric, citric, tartaric, phosphoric, lactic, pyruvic, acetic, succinic, oxalic, fumaric, maleic, oxaloacetic, methanesulphonic, ethanesulphonic, benzenesulphonic, and isethionic acids.

Pharmaceutical formulations may be adapted for administration by any appropriate route, for example by the oral (including buccal or sublingual), rectal, nasal, vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets.

Pharmaceutical formulations adapted for oral administration may be presented as discrete units such as capsules or tablets; powders or granules; solutions or suspensions in aqueous or non-aqueous liquids; edible foams or ships; or oil-in-water liquid emulsions or water-in-oil liquid emulsions.

The unit dosage form of the invention can be given one, two, three, four or more times a day in accordance with the total daily dosages recommended hereinbefore. Thus for a four times daily treatment, a unit dosage would suitably contain 60 mg to 1500 mg tyrosine or derivative (i.e. 240 mg to 6000 mg divided by 4) and 0.5 mg to 25 mg of iron present as an iron containing compound. Preferably it would also contain 0.5 mg to 20 mg vitamin B6 and/or 0.01 mg to 2.5 mg folate and/or 0.5 mg to 125 mg vitamin B3 and/or 0.5 mg to 20 mg of zinc present as a zinc containing compound. Similarly if a three times daily dose was administered, then the unit dosage form would be a multiple of three of the total daily dosage.

Further aspects of the invention are as follows:
a) a method for the treatment of Parkinson's disease or depression which comprises administering in therapeutic amounts to the patient separately, sequentially or as a combined product, the combination of tyrosine or a pharmacologically acceptable derivative thereof and an iron containing compound;
b) an anti-depressant or anti-Parkinson's disease pharmaceutical composition (such as a tablet, powder or capsule) comprising tyrosine or a pharmacologically acceptable derivative thereof, an iron containing compound and a pharmaceutically acceptable carrier;

As a broader principle to the combinations outlined hereinbefore, it is proposed that tyrosine alone, zinc alone, and iron alone will be useful in the treatment of depression (although a combination is preferred).

Accordingly, there is further provided:
c) use of a compound selected from the group consisting of tyrosine or a pharmacologically acceptable derivative thereof, an iron containing compound, and a zinc containing compound in the preparation of a medicament for the treatment or prophylaxis of depression (the total daily dosages dosage forms and the preferred actives are as given hereinbefore); and
d) a method for the treatment or prophylaxis of depression comprising administering to the patient, therapeutic amounts of a compound selected from the group consisting of tyrosine or a pharmacologically acceptable derivative thereof, an iron containing compound and a zinc containing compound.

For the treatment of depression, preferably there is also a component present which produces a sustained high level of blood sugar.

An example of a tablet or capsule in accordance with the invention for the treatment of Parkinson's disease and depression has the following active ingredients:

| | |
|---|---|
| 600.00 mg | L-Tyrosine |
| 13.50 mg | Ferrous sulphate (dried) |
| 12.50 mg | Zinc sulphate (dried) |
| 5.00 mg | Nicotinamide |
| 0.60 mg | Pyridoxine hydrochloride |
| 0.10 mg | Folic acid |

A total of four tablets may be taken every day by the patient for several months until a beneficial improvement is obtained. The dosages are based on average 70 kg adult, and so a heavier adult may benefit from higher daily dosages. Similarly Parkinson's disease patients who have previously been treated with L-dopa may benefit from higher dosages.

What is claimed is:

1. A pharmaceutical composition comprising a tyrosine compound and an iron containing compound, said tyrosine compound being selected from the group consisting of tyrosine and pharmacologically acceptable derivatives thereof and being the majority constituent of the composition.

2. A pharmaceutical composition as claimed in claim 1 for combined, sequential or simultaneous administration for the treatment or prophylaxis of a condition selected from the group consisting of Parkinson's disease and depression wherein the condition is not due to a deficiency of the immune system.

3. A pharmaceutical product comprising as the sole active agents a tyrosine compound selected from the group consisting of tyrosine and pharmacologically acceptable derivatives thereof as the largest constituent, an iron containing compound, and, optionally, one or more compounds selected from the group consisting of vitamin B6, folates, vitamin B3, and zinc containing compounds for combined, sequential or simultaneous administration for the treatment or prophylaxis of a condition selected from the group consisting of Parkinson's disease and depression.

4. The pharmaceutical product according to claim 3 comprising 60 to 1500 mg tyrosine compound, 0.5 to 25 mg iron as the iron-containing compound, and, optionally, one or more of 0.05 to 60 mg vitamin B6, 0.01 to 2.5 mg folate, 0.5 to 125 mg vitamin B3, and 0.5 to 20 mg zinc as the zinc-containing compound.

5. The pharmaceutical product according to claim 4 comprising 300 to 900 mg tyrosine compound, 2.5 to 7.5 mg iron as the iron-containing compound, and, optionally, one or more of 0.3 to 0.9 mg vitamin B6, 0.05 to 0.2 mg folate, 2.5 to 7.5 mg vitamin B3, and 2.5 to 7.5 mg zinc as the zinc-containing compound.

6. The pharmaceutical product according to claim 3 comprising as the sole active agents the tyrosine compound, the iron containing compound, a vitamin B6, a folate, a vitamin B3, and the zinc containing compound.

7. The pharmaceutical product according to claim 6 comprising as the sole active agents 60 to 1500 mg L-tyrosine, 0.5 to 25 mg iron as ferrous sulphate, 0.05 to 60 mg pyridoxine hydrochloride, 0.01 to 2.5 mg folic acid, 0.5 to 125 mg nicotinamide, and 0.5 to 20 mg zinc as zinc sulphate.

8. The pharmaceutical product according to claim 7 comprising as the sole active agents 300 to 900 mg L-tyrosine, 2.5 to 7.5 mg iron as ferrous sulphate, 0.3 to 0.9 mg pyridoxine hydrochloride, 0.05 to 0.2 mg folic acid, 2.5 to 7.5 mg nicotinamide, and 2.5 to 7.5 mg zinc as zinc sulphate.

9. A pharmaceutical composition comprising a tyrosine compound selected from the group consisting of tyrosine and pharmacologically acceptable derivatives thereof as the largest constituent together with an iron containing compound for combined, sequential or simultaneous administration for the treatment or prophylaxis of a condition selected from the group consisting of Parkinson's disease and depression, wherein the tyrosine compound is present in an amount of at least 60 mg and constitutes the majority of the composition and the composition comprises vitamin B3.

10. A pharmaceutical composition consisting essentially of a tyrosine compound selected from the group consisting of tyrosine and pharmacologically acceptable derivatives thereof; an iron containing compound; and, optionally, one or more compounds selected from the group consisting of vitamin B6, folates, vitamin B3, and zinc containing compounds; with one or more carriers or excipients.

11. A pharmaceutical composition according to claim 10 wherein the tyrosine compound is the majority constituent, said composition being for combined, sequential or simultaneous administration for the treatment or prophylaxis of a condition selected from the group consisting of Parkinson's disease and depression wherein the condition is not due to a deficiency of the immune system.

12. A pharmaceutical composition according to claim 10 comprising 60 to 1500 mg tyrosine compound selected from the group consisting of tyrosine and pharmacologically acceptable derivatives thereof; 0.5 to 25 mg iron as an iron-containing compound; and, optionally, one or more of 0.05 to 60 mg vitamin B6, 0.01 to 2.5 mg folate, 0.5 to 125 mg vitamin B3, and 0.5 to 20 mg zinc as a zinc-containing compound.

13. The pharmaceutical composition according to claim 12 comprising 300 to 900 mg tyrosine compound, 2.5 to 7.5 mg iron as the iron-containing compound, and, optionally, one or more of 0.3 to 0.9 mg vitamin B6, 0.05 to 0.2 mg folate, 2.5 to 7.5 mg vitamin B3, and 2.5 to 7.5 mg zinc as the zinc-containing compound.

14. The pharmaceutical composition according to claim 12 consisting essentially of the tyrosine compound, an iron containing compound, a vitamin B6, a folate, a vitamin B3, and a zinc containing compound, with one or more carriers or excipients.

15. The pharmaceutical composition according to claim 12 wherein the tyrosine compound is L-tyrosine.

16. The pharmaceutical composition according to claim 15 comprising 60 to 1500 mg L-tyrosine, 0.5 to 25 mg iron as ferrous sulphate, 0.05 to 60 mg pyridoxine hydrochloride, 0.01 to 2.5 mg folic acid, 0.5 to 125 mg nicotinamide, and 0.5 to 20 mg zinc as zinc sulphate.

17. The pharmaceutical composition according to claim 16 comprising 300 to 900 mg L-tyrosine, 2.5 to 7.5 mg iron as ferrous sulphate, 0.3 to 0.9 mg pyridoxine hydrochloride, 0.05 to 0.2 mg folic acid, 2.5 to 7.5 mg nicotinamide, and 2.5 to 7.5 mg zinc as zinc sulphate.

18. The pharmaceutical composition according to claim 10, wherein the tyrosine compound is present in an amount of at least 60 mg and constitutes the majority of the composition and the composition comprises vitamin B3.

19. A method for the treatment or prophylaxis of a condition selected from Parkinson's disease and depression comprising combined, sequential or simultaneous administration to a patient of a tyrosine compound selected from the group consisting of tyrosine and pharmacologically acceptable derivatives thereof as the largest amount of an active compound and an iron containing compound.

20. The method according to claim 19 wherein the condition is not due to a deficiency of the immune system.

21. A method for the treatment or prophylaxis of a condition selected from Parkinson's disease and depression comprising administering to a patient a pharmaceutical product comprising as the sole active agents a tyrosine compound selected from the group consisting of tyrosine and pharmacologically acceptable derivatives thereof as the largest constituent, an iron containing compound, and, optionally, one or more compounds selected from the group consisting of vitamin B6, folates, vitamin B3, and zinc containing compounds.

22. The method according to claim 21 wherein the pharmaceutical product comprises 60 to 1500 mg tyrosine compound, 0.5 to 25 mg iron as the iron-containing compound, and, optionally, one or more of 0.05 to 60 mg vitamin B6, 0.01 to 2.5 mg folate, 0.5 to 125 mg vitamin B3, and 0.5 to 20 mg zinc as the zinc-containing compound.

23. The method according to claim 22 wherein the pharmaceutical product comprises 300 to 900 mg tyrosine compound, 2.5 to 7.5 mg iron as an iron-containing compound, and, optionally, one or more of 0.3 to 0.9 mg vitamin B6, 0.05 to 0.2 mg folate, 2.5 to 7.5 mg vitamin B3, and 2.5 to 7.5 mg zinc as the zinc-containing compound.

24. The method according to claim 21 wherein the pharmaceutical product comprises as the sole active agents the tyrosine compound, the iron containing compound, a vitamin B6, a folate, a vitamin B3, and the zinc containing compound.

25. The method according to claim 24 wherein the pharmaceutical product comprises as the sole active agents 60 to 1500 mg L-tyrosine, 0.5 to 25 mg iron as ferrous sulphate, 0.05 to 60 mg pyridoxine hydrochloride, 0.01 to 2.5 mg folic acid, 0.5 to 125 mg nicotinamide, and 0.5 to 20 mg zinc as zinc sulphate.

26. The method according to claim 25 wherein the pharmaceutical product comprises as the sole active agents 300 to 900 mg L-tyrosine, 2.5 to 7.5 mg iron as ferrous sulphate, 0.3 to 0.9 mg pyridoxine hydrochloride, 0.05 to 0.2 mg folic acid, 2.5 to 7.5 mg nicotinamide, and 2.5 to 7.5 mg zinc as zinc sulphate.

27. A method for the treatment or prophylaxis of a condition selected from Parkinson's disease and depression comprising administering to a patient a pharmaceutical composition consisting essentially of a tyrosine compound selected from the group consisting of tyrosine and pharmacologically acceptable derivatives thereof; an iron containing compound; and, optionally, one or more compounds selected from the group consisting of vitamin B6, folates, vitamin 3, and zinc containing compounds; with one or more carriers or excipients.

28. A method according to claim 19 wherein the pharmaceutical composition comprises 60 to 1500 mg tyrosine compound selected from the group consisting of tyrosine and pharmacologically acceptable derivatives thereof, 0.5 to 25 mg iron as an iron-containing compound; and, optionally, one or more of 0.05 to 60 mg vitamin B6, 0.01 to 2.5 mg folate, 0.5 to 125 mg vitamin B3, and 0.5 to 20 mg zinc as a zinc-containing compound.

29. The method according to claim 28 wherein the pharmaceutical composition comprises 300 to 900 mg tyrosine compound, 2.5 to 7.5 mg iron as the iron-containing compound, and, optionally, one or more of 0.3 to 0.9 mg vitamin B6, 0.05 to 0.2 mg folate, 2.5 to 7.5 mg vitamin B3, and 2.5 to 7.5 mg zinc as the zinc-containing compound.

30. The method according to claim 28 wherein the pharmaceutical composition consists essential of the tyrosine compound, the iron containing compound, a vitamin B6, a folate, a vitamin B3, and a zinc containing compound, with one or more carriers or excipients.

31. The method according to claim 28 wherein the pharmaceutical composition comprises 60 to 1500 mg L-tyrosine, 0.5 to 25 mg iron as ferrous sulphate, 0.05 to 60 mg pyridoxine hydrochloride, 0.01 to 2.5 mg folic acid, 0.5 to 125 mg nicotinamide, and 0.5 to 20 mg zinc as zinc sulphate.

32. The method according to claim 31 wherein the pharmaceutical composition comprises 300 to 900 mg L-tyrosine, 2.5 to 7.5 mg iron as ferrous sulphate, 0.3 to 0.9 mg pyridoxine hydrochloride, 0.05 to 0.2 mg folic acid, 2.5 to 7.5 mg nicotinamide, and 2.5 to 7.5 mg zinc as zinc sulphate.

* * * * *